United States Patent [19]

Barrett et al.

[11] Patent Number: 4,835,278

[45] Date of Patent: May 30, 1989

[54] PREPARATION OF PIPERIDINYLCYCLOPENTYLHEPTENOIC ACID DERIVATIVES

[75] Inventors: Roger Barrett, Camberley; Clive A. Meerholz, Buntingford; Brian D. Judkins, Ware, all of England

[73] Assignee: Glaxo Group Limited, London, England

[21] Appl. No.: 7,670

[22] Filed: Jan. 28, 1987

[30] Foreign Application Priority Data

Jan. 28, 1986 [GB] United Kingdom ............... 8601985

[51] Int. Cl.$^4$ .................... C07D 211/34; C07C 35/06; C07C 37/00; C07C 29/132
[52] U.S. Cl. .................... 546/239; 568/838; 568/772; 568/830
[58] Field of Search ............... 546/239; 568/838, 772, 568/830

[56] References Cited

U.S. PATENT DOCUMENTS

| 4,342,756 | 8/1982 | Collington et al. | 546/239 |
| 4,409,213 | 10/1983 | Collington et al. | 546/239 |
| 4,482,549 | 11/1984 | Collington et al. | 546/239 |

FOREIGN PATENT DOCUMENTS

| 2097397 | 4/1982 | United Kingdom . |
| 2127406 | 9/1983 | United Kingdom . |
| 2129796 | 10/1983 | United Kingdom . |

OTHER PUBLICATIONS

Andre L. Gemal et al., J. Am. Chem. Soc. (1981) vol. 103, pp. 5454–5459.

*Primary Examiner*—Richard L. Raymond
*Assistant Examiner*—Mark W. Russell
*Attorney, Agent, or Firm*—Bernard, Rothwell & Brown

[57] ABSTRACT

A process is described for the preparation of a compound of formula (2)

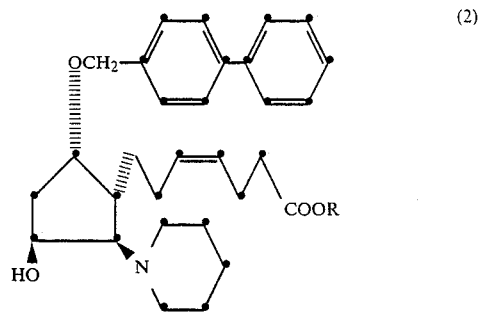

(wherein R is a $C_{1-6}$ alkyl or a $C_{7-20}$ aralkyl group) and the salts thereof, which comprises reducing a compound of formula (3)

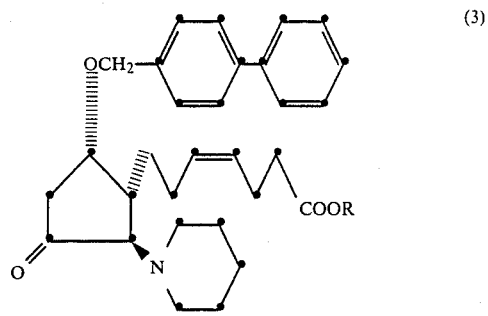

(or a salt thereof), using a reducing system comprising borohydride ions and metal ions selected from lanthanide ions, alkaline earth metal ions or yttrium ions in solution. The reduction system may be provided by a borohydride (e.g. $NaBH_4$) and a metal salt (e.g. $CeCl_3$).

The ester (2) may then if desired be hydrolyzed to give the parent acid.

22 Claims, No Drawings

PREPARATION OF PIPERIDINYLCYCLOPENTYLHEPTENOIC ACID DERIVATIVES

This invention relates to an improved process for the preparation of [1R-[1α(Z),2β,3β,5α]]-(+)-7-[5-[[(1,1'-biphenyl)-4-yl]methoxy]-3-hydroxy-2-(1-piperidinyl)-cyclopentyl]-4-heptenoic acid and salts thereof.

Our British Patent Specifications Nos. 2097397, 2127406 and 2129796 describe inter alia [1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoic acid and methods for its preparation. The compound is a potent antagonist of the actions of thromboxane $A_2$, and, in particular, it inhibits thromoboxane $A_2$ and endoperoxide mediated aggregation of blood platelets.

[1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoic acid may be represented by formula (1):

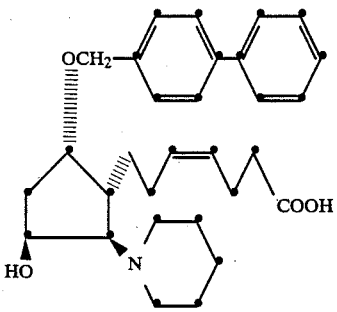

Formula (1) and the various other formulae used herein are to be understood to relate to the 1R enantiomers of the compounds concerned.

Although a number of different approaches for the synthesis of the compound of formula (1) are described in the above-mentioned patent specifications, we have found that it is particularly advantageous to arrange the synthesis such that in a final step the compound is prepared from an ester of formula (2):

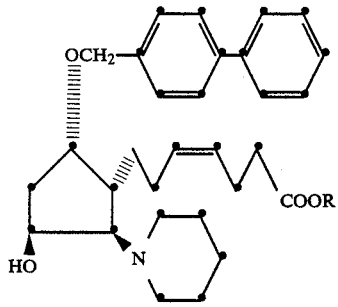

where COOR is for example an alkoxycarbonyl group.

The esters of formula (2) are most conveniently prepared by reduction of a ketone of formula (3)

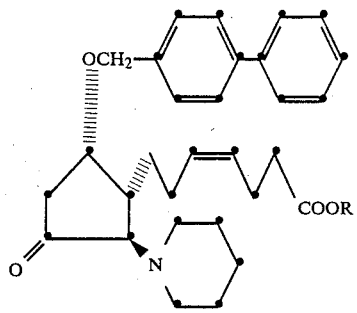

Reducing agents which stereoselectively reduce the keto group are required for this reaction to avoid the preparation of significant amounts of the unwanted epimeric esters of formula (2) [i.e. esters of formula (2) in which the hydroxyl group is in the opposite configuration to that shown in the formula]. Those reducing agents that have previously been described are diisobutylaluminium-2,6-di-t-butyl-4-methylphenoxide, lithium trisiamylborohydride, 2,6-di-tert-butyl-4-methylphenoxymagnesium hydride and potassium triisopropoxyborohydride.

We have now found a more convenient reducing system which provides very high yields of the desired ester of formula (2) relative to the corresponding unwanted epimer. The present improved process is advantageously convenient since the reagents are readily handled, and the process is relatively inexpensive to operate.

Thus in one aspect of the present invention we provide a process for the preparation of a compound of formula (2)

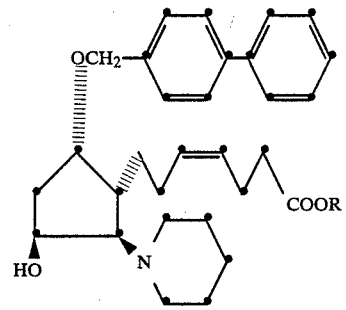

(wherein R is a $C_{1-6}$ alkyl or a $C_{7-20}$ aralkyl group) and the salts thereof, which involves reducing a compound of formula (3)

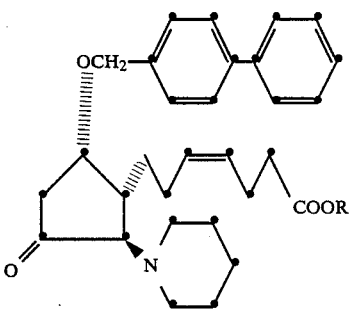

(wherein R is a $C_{1-6}$ alkyl or $C_{7-20}$ aralkyl group) or a salt thereof, using a reducing system comprising borohydride ions and suitable metal ions selected from lanthanide ions, alkaline earth metal ions or yttrium ions in solution.

When the group R is an alkyl group it may be for example a methyl, ethyl or t-butyl group. When R is an aralkyl group it may be for example a benzyl, benzhydryl or trityl group. Suitable salts of the compounds of formula (3) include acid addition salts, for example hydrochlorides.

The borohydride ions may conveniently be obtained by dissolving a suitable alkali or alkaline earth metal borohydride in an appropriate solvent. Examples of alkali metal borohydrides include lithium borohydride, sodium borohydride, sodium cyanoborohydride and sodium trifluoroacetoxy borohydride. Examples of alkaline earth metal borohydrides include calcium borohydride. The use of alkali metal borohydrides is generally preferred. The borohydride ions are preferably obtained from sodium borohydride.

Examples of lanthanide metal ions include lanthanum and cerium ions. Examples of alkaline earth metal ions include magnesium, strontium or barium ions, or more particularly calcium ions.

Preferred metal ions for use in the process of the invention include lanthanum, cerium and yttrium ions. We have found cerium ions to be particularly useful.

The metal ions may be generated in solution from a suitable metal salt. Any suitable metal salt of an acid may be used, eg a metal halide such as a chloride, bromide or iodide. A particularly useful metal salt for the reaction is cerium trichloride.

Suitable solvents for use in the reduction include alcohols e.g. methanol or ethanol or dimethylsulphoxide or mixtures of alcohols with other solvents e.g. ethers such as tetrahydrofuran or bis(2-methoxyethyl) ether or halogenated hydrocarbons e.g. dichloromethane. The reduction may be carried out at a temperature within the range −20° to +60°, preferably at −20° to +40° and more conveniently at 0° C. to ambient.

Preferably at least 1 molar equivalent of metal ions are present in the reducing system, or two or more metal salts giving at least 1 molar equivalent of the total metal ions in solution may also be used.

In a preferred aspect, we provide a process for the preparation of a compound of formula (2) which comprises reducing a compound of formula (3) or a salt thereof using an alkali metal borohydride, especially sodium borohydride, in the presence of a lanthanide, yttrium, barium, strontium, calcium or magnesium salt in a suitable solvent. The reduction is preferably effected using sodium borohydride in the presence of a lanthanum, yttrium, or especially, a cerium salt. A particularly preferred reducing system is sodium borohydride and cerium trichloride.

If desired, an ester of formula (2) obtained according to the process of the invention may be isolated in the form of a salt, for example an acid addition salt e.g. a hydrochloride, by reaction of the free base of the ester with an appropriate acid e.g. hydrochloric acid.

We have found the process according to the invention to be especially suitable for the preparation of a compound of formula (2) in which R is a methyl group. Thus in a particularly preferred aspect of the invention we provide a process for the preparation of a compound of formula (2) wherein R is a methyl group, or a salt thereof, which comprises reducing a compound of formula (3) wherein R is a methyl group, or a salt thereof, using the reagents and conditions described above.

The ester of formula (3) wherein R is a methyl group is a novel and particularly useful intermediate and forms a further aspect of the invention.

The intermediate esters of formula (3) may be prepared by the methods described in British Patent Specification No. 2097397.

The esters of formula (2) may be converted to the compound of formula (1) or a salt thereof by conventional acid or base hydrolysis procedures. Thus according to another aspect of the invention we provide a process for the preparation of a compound of formula (1) or a salt thereof which comprises the steps of (i) reducing a compound of formula (3) or a salt thereof to yield an ester of formula (2) or a salt thereof and (ii) hydrolysing the said ester or a salt thereof to obtain the acid of formula (1) and optionally treating said acid to obtain a salt thereof.

This process is particularly suitable for the preparation of the hydrochloride salt of the compound of formula (1). It is especially advantageous to use the methyl ester of formula (3), i.e. wherein R is a methyl group, as the starting material for the process.

The reduction step may be performed using the reagents and conditions as described above. The hydrolysis step is advantageously carried out using a base such as an inorganic base e.g. sodium hydroxide in a suitable solvent such as an aqueous alcohol e.g. aqueous methanol.

The acid of formula (1) so obtained may be converted where desired to a salt by reaction with an appropriate acid. Thus for example the hydrochloride salt may be prepared by reaction of the free base of the acid of formula (1) with hydrochloric acid.

The following Examples illustrate the invention. All temperatures are in °C. In the following examples high performance liquid chromatography (h.p.l.c.) was carried out using Spherisorb S5 CN, mobile phase 0.1M ammonium acetate/methanol (3:97). The work-up procedures, systems A-D, referred to in the examples are as follows:

System A: The mixture was evaporated in vacuo and the residue partitioned between 2N hydrochloric acid (70 ml) and dichloromethane (2×70 ml). The combined organic extracts were washed with 2N hydrochloric acid and evaporated in vacuo.

System B: The mixture was partitioned between dichloromethane (20 ml) and 2N hydrochloric acid (10 ml). The organic extract was dried ($Na_2SO_4$) and evaporated.

System C: The mixture was poured into phosphate buffer (pH 7, 15 ml) and extracted with dichloromethane (2×10 ml). The combined organic extracts were dried ($Na_2SO_4$) and evaporated in vacuo.

System D: The mixture was partitioned between water (15 ml) and ethyl acetate (10 ml). The organic extract was dried ($Na_2SO_4$) and evaporated in vacuo.

The preparation of [1R-[1α(Z),2β,3α,5α]]-(+)-7-[5-[[(1,1′-biphenyl)-4-yl]methoxy]-3-hydroxy-2-(1-piperidinyl)cyclopentyl]-4-heptenoic acid is described in European patent application Publication No. 127930.

INTERMEDIATE 1

[1R-[1α(Z),2β,3α,5α]]-(+)-Methyl 7-[5-[[(1,1'-Biphenyl)-4-yl)methoxy]-3-hydroxy-2-(1-piperidinyl)cyclopentyl]-4-heptenoate, hydrochloride A solution of [1R-[1α(Z),2β,3α,5α]]-(+)-7-[5-[[(1,1'-biphenyl)-4-yl]methoxy]-3-hydroxy-2-(1-piperidinyl)-cyclopentyl]-4-heptenoic acid (1.337 g) in methanol (20 ml) containing concentrated sulphuric acid (0.4 ml) was kept at 20° for 3 h then poured into 2N Na$_2$CO$_3$ (75 ml) and extracted with ethyl acetate (3×50 ml). The combined extracts were dried and evaporated and the residue was purified by chromatography using 9:1 ethyl acetate-methanol as eluent to give the title compound, base as an oil (0.867 g). A portion of the oil (0.445 g) in dichloromethane (3 ml) was treated with an excess of ethereal hydrogen chloride and the solvents were removed in vacuo. The residue was triturated with ether and then crystallised from ethyl acetate-methanol to give the title compound (0.253 g) m.p. 130°–133°, $[\alpha]_D^{24}$ +56.8° (CHCl$_3$).

INTERMEDIATE 2

[1R-[1α(Z),2β,5α]]-(−)-Methyl 7-[5-[[(1,1'-Biphenyl)-4-yl]methoxy]-3-oxo-2-(1-piperidinyl)cyclopentyl]-4-heptenoate To a solution of Intermediate 1 (37.15 g) in dichloromethane (150 ml) was added triethylamine (74 ml) and the solution cooled to −5° under nitrogen. A solution of pyridine-sulphur trioxide complex (53.71 g) in dimethylsulphoxide (150 ml) was added over a period of 0.5 h. After 3 h the reaction mixture was poured into cold water (300 ml) at <10° and the organic layer separated. The aqueous layer was extracted with dichloromethane (300 ml) and the combined organic extracts washed with 1M citric acid (2×300 ml, at 10°) and water (200 ml), dried (Na$_2$SO$_4$) and evaporated in vacuo. The residue was co-evaporated with t-butyl methyl ether (100 ml) and seeded, causing crystallisation of the title compound (36.94 g) as an off-white solid. A sample was recrystallised from methanol to give the title compound m.p. 57°–58°, $[\alpha]_D^{20}$ −21.9° (CHCl$_3$).

PREPARATION OF

[1R-[1α(Z),2β,3β,5α]]-(+)-Methyl 7-[5-[[(1,1'-biphenyl)-4-yl]methoxy]-3-hydroxy-2-(1-piperidinyl)cyclopentyl]-4-heptenoate, hydrochloride

EXAMPLE 1

Sodium borohydride (25 mg) was added in small portions to a solution of Intermediate 2 (0.30 g) and cerium trichloride heptahydrate (0.25 g) in a mixture of tetrahydrofuran (1.2 ml) and methanol (1.8 ml). The temperature of the reaction mixture was kept between 0° and 5° during the course of the addition. After the last of the sodium borohydride had been added the reaction mixture was stirred at 5° for a further 10 minutes and worked up according to system B. Analysis of the product by h.p.l.c. revealed that the title compound had been obtained in a ratio of the 3-β and 11-α epimers of 96.6:3.4.

EXAMPLE 2

The title compound was prepared according to the method of Example 1 using a mixture of cerium trichloride heptahydrate (106 mg) and calcium chloride dihydrate (337 mg) in place in cerium trichloride heptahydrate. Analysis of the product by h.p.l.c. revealed that the desired compound had been obtained in a ratio of the 3-β and 11-α epimers of 95.6:4.4.

EXAMPLE 3

A suspension of sodium trifluoroacetoxyborohydride (ca. 1 mMole, freshly prepared from trifluoroacetic acid and sodium borohydride in tetrahydrofuran, 0.5 ml) was added dropwise at 0° to a stirred solution of Intermediate 2 (0.50 g) and cerium trichloride heptahydrate (0.38 g) in dichloromethane (1 ml) and methanol (4 ml). The temperature of the reaction mixture was kept at 0° during the addition. The mixture was stirred at 0° for 10 minutes and worked up according to System A. Analysis of the product by h.p.l.c. revealed that the title compound had been obtained in a ratio of the 3-β and 11-α epimers of 97.1:2.9.

EXAMPLE 4

The title compound was prepared according to the method of Example 1 using lithium borohydride (23 mg) in tetrahydrofuran (0.5 ml) in place of sodium borohydride and the reaction mixture was worked up according to System A. Analysis of the product by h.p.l.c. revealed that the title compound had been obtained in a ratio of the 3-β and 3-α epimers of 96.2:3.8.

EXAMPLE 5

Calcium iodide tetrahydrate (337 mg) was added to a solution of Intermediate 2 (0.42 g) in dichloromethane (0.85 ml) and methanol (3.4 ml) and the mixture cooled to 5°. Sodium borohydride (33 mg) was added at a rate so as to maintain a temperature of 0° to 5°. After the last of the sodium borohydride had been added the reaction mixture was stirred at 5° for a further 0.5 h, and worked up according to System B. Analysis of the product by h.p.l.c. revealed that the title compound had been obtained in a ratio of the 3-β and 3-α epimers of 86.8:13.2

EXAMPLE 6

The free base of the title compound was prepared according to the method of Example 1 using strontium chloride hexahydrate (140 mg) in place of cerium trichloride heptahydrate and the reaction mixture was worked up using System C. Analysis of the product by h.p.l.c. revealed that the free base of the title compound had been obtained in a ratio of the 3-β and 3-α epimers of 83.4:16.6.

EXAMPLE 7

A solution of magnesium chloride hexahydrate (83 mg) in methanol (1.2 ml) was added to a solution of Intermediate 2 (220 mg) in tetrahydrofuran (0.8 ml) and the mixture cooled to 0°. Sodium borohydride (16 mg) was added at a rate so as to maintain a reaction temperature of 0° to 5°. After the last of the sodium borohydride had been added the reaction mixture was stirred at 5° for a further 10 minutes, and worked up using System C. Analysis of the product by h.p.l.c. revealed that the free base of the title compound had been obtained in ratio of the 3-β and 3-α epimers of 82.7:17.3.

EXAMPLE 8

The free base of the title compound was prepared according to the method of Example 7 using calcium chloride dihydrate (0.07 g) in place of magnesium chloride hexahydrate. Analysis of the product by h.p.l.c.

revealed that the free base of the title compound had been obtained in a ratio of the 3-$\beta$ and 3-$\alpha$ epimers of 85.9:14.1.

EXAMPLE 9

The free base of the title compound was prepared according to the method of Example 7 using lanthanum trichloride heptahydrate (0.26 g) in place of magnesium chloride hexahydrate. Analysis of the product by h.p.l.c. revealed that the free base of the title compound had been obtained in a ratio of the 3-$\beta$ and 3-$\alpha$ epimers of 96.4:3.6.

EXAMPLE 10

The free base of the title compound was prepared according to the method of Example 7 using yttrium trichloride hexahydrate (0.155 g) in place of magnesium chloride hexahydrate and the reaction mixture was worked up using System D. Analysis of the product revealed that the free base of the title compound had been obtained in a ratio of the 3-$\beta$ and 3-$\alpha$ epimers of 96.4:3.6.

EXAMPLE 11

Cerium trichloride heptahydrate (75.64 g) was dissolved in methanol (800 ml), cooled to 5° and added to a stirred solution of Intermediate 2 (82.0 g) in dichloromethane (300 ml total volume) at 5° under a nitrogen atomosphere. The solution was stirred at 5° for 5 min and then treated with sodium borohydride (4.63 g) in small portions over 0.5 h. The reaction mixture was quenched with 2N hydrochloric acid (1000 ml), diluted with dichloromethane (800 ml) and the organic phase was washed with 2N hydrochloric acid (3×800 ml), followed by brine solution (200 ml) and concentrated before dilution with iso-propyl acetate (900 ml). This solution was washed with 2N sodium carbonate (3×800 ml), 2N hydrochloric acid (800 ml) and brine solution (400 ml). The organic solution was concentrated and the residue diluted with more iso-propyl acetate (600 ml) before filtration and final concentration to promote crystallisation. The suspension was filtered to give the title compound (72.3 g) as a cream solid, m.p. 118°–120°, $[\alpha]_D + 65°$ (CHCl$_3$).

EXAMPLE 12

[1R-[1$\alpha$(Z),2$\beta$,3$\beta$,5$\alpha$]]-(+)-7-[5-[[(1,1'-Biphenyl)-4-yl]methoxy]-3-hydroxy-2-(1-piperidinyl)cyclopentyl]-4-heptenoic acid, hydrochloride.

A suspension of the product of Example 11 (5.0 g) in methanol (12.5 ml) and 5N sodium hydroxide (7.5 ml) was stirred for 18 h at ambient temperature. The solution was cooled to 5°, diluted with dichloromethane (25 ml) and the mixture acidified to pH 2 with 2N hydrochloric acid (21 ml). The phases were separated, the aqueous phase back-extracted with dichloromethane (15 ml) and the combined organic extracts concentrated to approximately half the original volume. The residue was filtered through Hyflo and the Hyflo washed with dichloromethane (10 ml). The combined filtrates were evaporated under nitrogen to approximately 10 ml and diluted with isopropanol (10 ml). The mixture was concentrated to leave a residual volume of 10 ml. The hot solution was diluted with isopropyl acetate (30 ml), cooled to 50° and seeded with authentic product. The mixture was allowed to cool to ambient temperature and stirred overnight. The suspension was cooled in an ice bath for 2 h, the solid filtered off, washed with isopropyl acetate (5 ml) and dried to afford the title compound as an off-white solid (4.16 g), m.p. 128°–129°, $[\alpha]_D^{20} = +66.7$ (CHCl$_3$).

We claim:

1. A process for the preparation of a compound of formula (2)

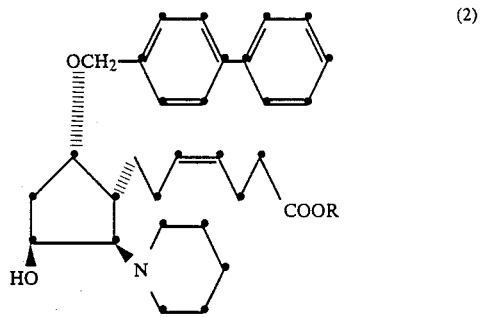

wherein R is a C$_{1-6}$ alkyl or a C$_{7-20}$ aralkyl group or a hydrochloride salt thereof, which comprises reducing a compound of formula (3)

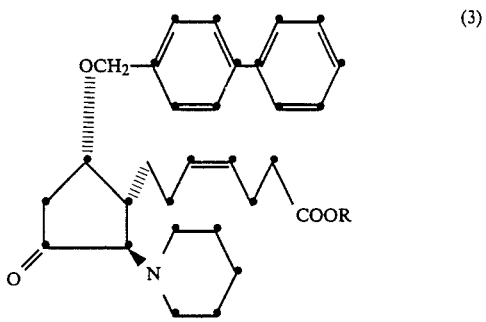

wherein R is a C$_{1-6}$ alkyl or is a C$_{7-20}$ aralkyl group or a hydrochloride salt thereof, using a reducing system comprising borohydride ions and metal ions selected from lanthanide ions, alkaline earth metal ions or yttrium ions in solution;

and thereafter converting the ester of formula (2) or a hydrochloride salt thereof into the corresponding acid of formula (1)

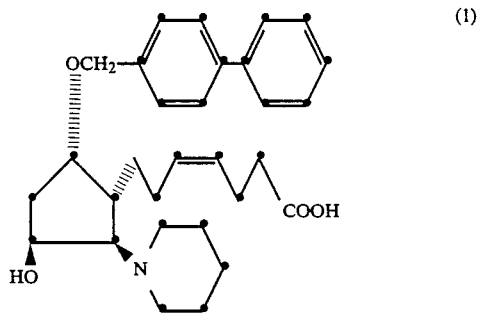

or a hydrochloride salt thereof.

2. A process according to claim 1 in which the metal ions are lanthanum, cerium or yttrium ions.

3. A process according to claim 1 in which the metal ions are cerium ions.

4. A process according to claim 1 in which the borohydride ions are provided by an alkali metal or alkaline earth metal borohydride and the metal ions are provided by a salt of the metal.

5. A process according to claim 4 in which the borohydride is sodium borohydride.

6. A process according to claim 4 in which the metal salt is a halide.

7. A process according to claim 4 in which the metal salt is cerium trichloride.

8. A process according to claim 1 in which the reduction is carried out in an alcoholic solvent.

9. A process according to claim 1 in which the solvent is a mixture of an alcohol with an ether or halogenated hydrocarbon and the reaction temperature is from 0° C. to ambient.

10. A process according to claim 1 in which R is a methyl group.

11. A process according to claim 1 in which the ester of formula (2) produced or a hydrochloride salt thereof is subjected to acid or base hydrolysis to form the acid of formula (1), which may then be treated with hydrochloric acid to form a hydrochloride salt.

12. A process according to claim 1 in which the methyl ester of formula (2) or a hydrochloride salt thereof is hydrolysed with sodium hydroxide to form the acid of formula (1), which is then treated with hydrochloric acid to form its hydrochloride salt.

13. A process for the preparation of a compound of formula (2)

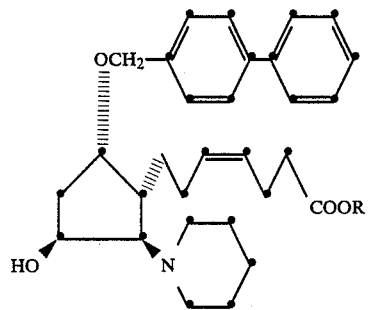

(2)

wherein R is a $C_{1-6}$ alkyl or a $C_{7-20}$ aralkyl group or a hydrochloride salt thereof, which comprises reducing a compound of formula (3)

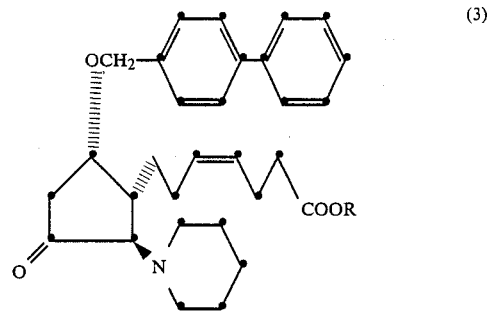

(3)

wherein R is a $C_{1-6}$ alkyl or $C_{1-20}$ aralkyl group or a hydrochloride salt thereof, using a reducing system comprising borohydride ions and metal ions selected from lanthanide ions, alkaline earth metal ions or yttrium ions in solution.

14. A process according to claim 13 in which the metal ions are lanthanum, cerium or yttrium ions.

15. A process according to claim 13 in which the metal ions are cerium ions.

16. A process according to claim 13 in which the borohydride ions are provided by an alkali metal or alkaline earth metal borohydride and the metal ions are provided by a salt of the metal.

17. A process according to claim 16 in which the borohydride is sodium borohydride.

18. A process according to claim 16, in which the metal salt is a halide.

19. A process according to claim 16 in which the metal salt is cerium trichloride.

20. A process according to claim 13 in which the reduction is carried out in an alcoholic solvent.

21. A process according to claim 13 in which the solvent is a mixture of an alcohol with an ether or halogenated hydrocarbon and the reaction temperature is from 0° C. to ambient.

22. A process according to claim 13 in which R is a methyl group.

* * * * *